United States Patent [19]

Mensi-Fattohi et al.

[11] Patent Number: 5,428,128
[45] Date of Patent: Jun. 27, 1995

[54] SITE SPECIFIC SYNTHESIS OF CONJUGATED PEPTIDES

[76] Inventors: Nahla Mensi-Fattohi, 151 Rutgers Rd., Piscataway, N.J. 08854; Christopher J. Molineaux, 115 E. 9th St., New York, N.Y. 10003; Robert G. L. Shorr, 28 Brookfall Rd., Edison, N.J. 08820

[21] Appl. No.: 313,547

[22] Filed: Sep. 27, 1994

Related U.S. Application Data

[63] Continuation of Ser. No. 80,457, Jun. 21, 1993, abandoned.

[51] Int. Cl.$^6$ .................. A61K 38/00; C07K 5/00; C07K 7/00; C07K 17/00
[52] U.S. Cl. .................. 530/302; 530/306; 530/307; 530/313; 530/324; 530/326; 530/327; 530/333; 530/334; 530/338
[58] Field of Search .............. 530/302, 306, 307, 313, 530/324, 326, 327, 333, 334, 338

[56] References Cited

U.S. PATENT DOCUMENTS

| | | | |
|---|---|---|---|
| 4,101,380 | 7/1978 | Rubinstein et al. | 195/63 |
| 4,179,337 | 12/1979 | Davis et al. | 435/181 |
| 4,904,582 | 2/1990 | Tullis | 435/6 |
| 4,904,584 | 2/1990 | Shaw | 435/69.4 |
| 5,049,656 | 9/1991 | Lewis et al. | 530/334 |
| 5,093,531 | 3/1992 | Sano et al. | 568/337 |
| 5,122,614 | 7/1992 | Zalipsky | 548/520 |

FOREIGN PATENT DOCUMENTS

| | | |
|---|---|---|
| 00340741 | 3/1989 | European Pat. Off. . |
| WO92/04384 | 3/1992 | WIPO . |
| WO92/16221 | 10/1992 | WIPO . |
| WO92/16555 | 10/1992 | WIPO . |

OTHER PUBLICATIONS

Kawasaki et al, Chem. Pharm. Bull., 39(12), pp. 3373–3375 (1991).
Mutter et al, The Peptides, vol. 2, pp. 285–332 (1979).
Zalipsky et al, Eyr. Polym. J., vol. 19, No. 12, pp. 1177–1183 (1983).
Lu, et al, Peptide Research, vol. 6, No. 3, (1993) p. 140.
Attassi, Journal of Protein Chemistry, vol. 10, No. 6 (1991) p. 623.
Zalipsky, Int. J. Peptide Protein Res. (30), 740–783 (1987).
Merrifield, Synthesis of a Tetrapeptide, vol. 85, 2149–2154 (1963).
Merrifield, Biochemistry (21), 5020–2031 (1993).

*Primary Examiner*—Jill Warden
*Assistant Examiner*—Sheela J. Huff

[57] ABSTRACT

Processes for synthesizing polypeptides containing substantially non-antigenic polymers, preferably poly(alkylene glycols) in specifically predetermined sites are disclosed. Polypeptides prepared by such processes acre also disclosed.

29 Claims, No Drawings

SITE SPECIFIC SYNTHESIS OF CONJUGATED PEPTIDES

This application is a continuation of application Ser. No. 08/080,457, filed Jun. 21, 1993, now abandoned.

BACKGROUND OF THE INVENTION

1. Field of Invention

The present invention relates to the controlled modification of peptide sequences with substantially non-antigenic polymeric moieties at one or more selected, predetermined positions.

2. Description of Related Art

U.S. Pat. No 4,904,584 describes modified proteins having naturally occurring amino acids such as lysine replaced with other amino acids to eliminate the random attachment of polyethylene glycol. The homogeneous conjugates are said to eliminate the need to separate the variety of conjugated species of the polypeptide. While the lysine depleted variants in theory would allow site specific polymer attachment, there is no guarantee that the described method actually achieves modification at all selected sites.

The ability to selectively attach moieties to specific sites on proteins and peptides continues. This is particularly the case with small peptides having, for example, fewer than thirty amino acids. These peptide modifications have been particularly troublesome and loss of activity has often resulted.

The covalent attachment of strands of a poly(alkylene glycol) to polypeptides is disclosed in U.S. Pat. No. 4,179,337. This reference discloses that proteins and enzymes modified with poly(ethylene glycols) have reduced immunogenicity and antigenicity and also have longer lifetimes in the bloodstream, compared to the unmodified compounds.

To effect covalent attachment of poly(ethylene glycol) (PEG) to a polypeptide, the hydroxyl end groups of the PEG must first be converted into reactive functional groups. This process is frequently referred to as "activation" and the product is called "activated PEG'. Methoxy poly(ethylene glycol) (mPEG), distally capped with a reactive functional group is often used. One such activated PEG is succinimidyl succinate derivative of PEG (SS-PEG). See also Abuchowski et al., Cancer Biochem. Biophys. 7:175–186 (1984) and commonly assigned U.S. Pat. No. 5,122,614 which discloses poly(ethylene glycol)-N-succinimide carbonate and its preparation.

Chem. Pharm. Bull. 39(12):3373–3375 (1991) discloses hybrids of a fibronectin-related tripeptide (Arg-Gly-Asp) and amino-poly(ethylene glycol) and their inhibitory effect on experimental metastasis in mice. The tripeptide was coupled with amino PEG by activating aspartic acid with dicyciohexylcarbodiimide (DCC)/1-hydroxybenzotriazole (HOBt). This method, however, is only useful for C-terminal modifications. Another limitation of this methodology is that C-terminal activation of peptides promotes racemization of neighboring amino acids. Such modifications would not be observed with glycine, all other amino acids would become racemic with consequent loss of activity.

Journal of Protein Chemistry 10(6):623–627 (199) describes a procedure for synthesis of peptides to monomethoxy poly(ethylene glycol) (mPEG) or polyvinyl alcohol (PVA) using a synthetic resin. This method, however, results in the conjugates having only one poller molecule coupled to the N-terminal of an otherwise unaltered peptide molecule.

While numerous references have reported that PEG conjugates are useful, for example in the medical arts, there often remains the need to control the sites at which the polymer attaches to maintain optimal biological activity. Uncontrolled polymeric conjugation sometimes results in polymeric strands attaching at sites that are critical for biological activity. This disadvantage can be especially acute for polypeptides having relatively short chains, since the possibilities for attachment are limited and the probability of attachment at a critical site correspondingly increases.

Accordingly, a need continues for a process which allows polymeric conjugation to polypeptides, yet avoids the loss of bioactivity.

SUMMARY OF THE INVENTION

The present invention relates to methods for synthesizing polypeptides containing substantially non-antigenic polymers in site-specific locations and to the polypeptides prepared by such processes.

More particularly, the method includes initiating synthesis of the polypeptide and introducing a substantially non-antigenic polymer at that point in the synthesis that corresponds to the predetermined site.

The synthesis is continued until the polypeptide is completed. Solid-phase synthesis techniques are preferred for carrying out the inventive process. In a preferred aspect of the invention, the polymer is conjugated to a facilitator moiety such as an amino acid or alkyl-containing group prior to being introduced into the polypeptide.

Preferred polymers are poly(alkylene glycols) such as poly(ethylene glycol) or PEG. The polymers are preferably functionalized on at least one end for covalent inclusion in the polypeptide. Examples of such polymers include mPEG-succinimidyl succinate and mPEG succinimidyl carbamates having molecular weights of around 5,000.

In another aspect, the invention relates to an alternative method of synthesizing a polypeptide containing a substantially non-antigenic polymer at a predetermined site. This embodiment includes initiating synthesis of the polypeptide; introducing a blocked facilitator moiety at that point in the synthesis that corresponds to the predetermined site; completing the synthesis; deblocking and conjugating the facilitator with the polymer.

In yet another aspect, the present invention relates to novel compositions of matter useful as intermediates in the practice of the present invention: N-α-Fmoc-N-ε-PEG-Lys and N-α-Fmoc-N-ε-PEG-β-Ala-Lys.

As a result of the present invention several polypeptides can be synthesized to include polymers. These polymers increase the length of time the polypeptide circulates in the bloodstream and substantially reduces the immunogenicity, if any, associated with the unmodified polypeptide. In addition the modified polypeptides described herein exhibit a controlled and predictable level of biological activity by virtue of their uniformity of manufacture.

DETAILED DESCRIPTION OF THE INVENTION

The present invention is directed to synthesizing polypeptides with substantially non-antigenic polymers at predetermined specific site(s). The modified polypeptides prepared thereby preferably include poly(alkylene glycols).

Synthesis of the polypeptide is initiated, such as with solid phase techniques, and the polymer is introduced at a point which corresponds to the predetermined site(s). Although solid phase techniques are preferred, it will be understood by those skilled in the art that alternative techniques are also contemplated.

The methods of the present invention can be carried out using any technique which allows the construction of polypeptides either sequentially or by other techniques which allows addition of moieties in a predetermined pattern or sequence. For example, techniques used to unite peptides or peptide sequences to each other can also be used so long as the technique can be modified to allow introduction of the polymer in the manner described herein.

The preferred poly(alkylene glycols) employed in the practice of the present invention include poly(ethylene glycol), poly(propylene glycol), and copolymers of poly(ethylene glycol) and poly(propylene glycol). Most preferred are polymers wherein one of the terminal hydroxyl groups of the poly(alkylene glycol) is capped, such as methoxy poly(ethylene glycol).

Hereinafter, for convenience, the poly(alkylene glycols) employed in the practice of the present invention will be designated "PAG". The term is intended to include compounds wherein R is hydrogen or alkyl. PEG refers to poly(ethylene glycol) and mPEG refers to methoxy poly(ethylene glycol).

The PAG does not have to be of a particular molecular weight, but it is preferred that the molecular weight be between about 200 and about 10,000; more preferably, between about 2,000 and about 7,500. Molecular weights of about 5,000 are most preferred. The choice of molecular weight of PAG is a matter of preference for the artisan and can be based, for example, on the nature of the particular modified polypeptide to be prepared, the number of sites selected for the polymer, etc.

Alternative substantially non-antigenic polymers that may be employed in the practice of the present invention include materials such as dextran, polyvinyl pyrrolidones, polysaccharides, starches, polyvinyl alcohols, polyacrylamides, or other similar non-immunogenic polymers. Those of ordinary skill in the art will realize that the foregoing are merely illustrative and not intended to restrict the type of polymeric substances suitable for use herein.

The process of the present invention includes synthesizing a peptide or polypeptide having biological activity or effect with a substantially non-antigenic polymer under conditions sufficient to effect conjugation while maintaining at least a portion of the desired biological activity.

In one preferred aspect of the invention, the polymer is introduced into the peptide sequence after being functionalized or activated for reaction and attachment to one or more amino acids. By activation, it is understood by those of ordinary skill in the art that the polymer is functionalized to include a desired reactive group. See, for example, U.S. Pat. Nos. 4,179,337 and 5,122,614, which are incorporated by reference herein. In these disclosures, the hydroxyl end groups of poly(alkylene glycols) are converted and activated into reactive functional groups.

In a particularly preferred aspect, the polymer is conjugated to a facilitator moiety prior to being introduced into the polypeptide sequence. The facilitator moiety is preferably an amino acid such as lysine, however, non-amino acid moieties are also contemplated. Within the aspect, there are included multifunctionalized organic moieties such as alkyls or substituted alkyls. Such moieties can be prepared to have a nucleophilic functional group such as an amine and an electrophilic group such as an acid as well as a suitably functinalized region for conjugating with the desired polymer or polymers.

The facilitator moieties allow easier inclusion of a polymer into the peptide sequence during synthesis. For example, PAGs coupled to facilitator amino acids or amino acid residues in polypeptides by means of suitable coupling agents are illustrative. A useful review of a number of coupling agents known in the art appears in Dreborg et al., *Critical Reviews in Therapeutic Drug Carrier Systems* 6(4): 315-165 (1990), see especially, pp. 317-320.

The terms "pegylated" and "pegylation" will be used herein to refer to the process of reacting a poly(alkylene glycol), preferably an activated poly(alkylene glycol), with a facilitator such as an amino acid i.e. lysine to form a covalent bond. Although "pegylation" is often carried out using poly(ethylene glycol) or derivatives thereof, such as methoxy poly(ethylene glycol), the term is not intended to be so limited here, but is intended to include any other useful poly(alkylene glycol), such as, for example poly(propylene glycol).

One particularly preferred activated PEG for the present invention is poly(ethylene glycol)-N-succinimide carbonate (SC-PEG) which is described in U.S. Pat. No. 5,122,614. This activated polymer forms stable, hydrolysis-resistant carbamate (urethane) linkages with amino groups. Isocyanate-activated PAG's are also of use. While the references incorporated herein ('614 and '337 patents) describe epsilon amino group modifications of lysine, other conjugation methods are also contemplated. Carbohydrate and/or acid group or other amino acid modifications are also within the scope of the present invention. Alternatively, the guanidino groups can be modified with phenyl glyoxal derivatives of methoxy poly(ethylene glycol) as disclosed, for example, in U.S. Pat. No. 5,093,531. Covalent linkage by any atom between the facilitator and polymer is possible. Moreover, non-covalent conjugation such as lipophilic or hydrophilic interactions are also contemplated. Where, as is often the case, crosslinking would be deemed undesirable, such crosslinking can be minimized or prevented by means known in the art. For example, a preferred means for preventing crosslinking is to preblock one end of the PAG, such as is done in the commercially available methoxy poly(ethylene glycol).

It will be readily apparent to those skilled in the art that other activated PAGs can also be employed in the practice of the present invention.

The conjugation reaction of the activated polymer and amino acid is carried out in a buffer, such as, ~0.1-~0.5 molar phosphate or borate solutions at a pH of from about 6.0 to about 9.3. The conjugate substituents are reacted with an appropriate amount of the polymer, which is typically present in amounts ranging from about equimolar to a several-fold molar excess over the amino acid or amino acid residue. The polymeric molar ratio excess will range from about 5 to about 125 and, preferably, from about 10 to about 50. The reaction is carried out at temperatures of from about 0° to 25° C. over time periods ranging from a few minutes to as long as twelve hours. Temperatures of from about 20° to about 25° C. are preferred and time periods of around one hour are usually sufficient to carry out the conjugation reaction.

Following the conjugation reaction, the desired product i.e. an amino acid-PEG conjugate, is recovered using known techniques and purified using column chromatography or similar apparatus, if necessary. The amino acid-polymer conjugates can then be inserted during synthesis of the peptide. The number of polypeptides that can be synthesized to contain polymers at a specific site by the methods of the present invention is vast. Virtually any peptide or polypeptide that can be synthesized can be synthesized to include one or more polymers. An illustrative, non-limiting list includes: dynorphin A, α-neo-endorphin, β-neo-endorphin, melittin, mastoparan, vasopressin, oxytocin, opioid peptides, kinins, angiotensin, luteinizing hormone releasing hormone, corticotropin releasing hormone, calcitonin, thyrotropin releasing hormone, phospholipase $A_2$ activating peptide (PLAP) and related polypeptides. The foregoing includes polypeptides having an affinity for a target in a range of from about $1 \times 10^{-7}$ to about $1 \times 10^{-11}$M.

Solid phase synthesis techniques are preferred in carrying out the method of the present invention. *J. Am. Chem. Soc.* 85:2149-2154 and/or *Biochemistry* 21:5020-5031 (1982) provide a general description of such techniques and are incorporated by reference herein.

Briefly, a first amino acid having a blocked amino group is covalently bonded to a cross-linked, insoluble polymeric resin, generally by formation of an ester linkage via the carboxyl group of the amino acid and a hydroxyl group on the polymeric resin. Blocking groups useful for the purpose may be any of a variety of organic moieties known in the art, the only requirement for their use being that the organic compound from which they are derived is reactive with the amino group of the amino acid and that the moiety formed by such reaction is inert with regard to the reactive groups of other molecules that will be present during the reaction to be performed. Two well known blocking groups that are preferred for use in the practice of the present invention are tert-butyloxycarbonyl (Boc) and 9-fluorenylmethyloxycarbonyl (Fmoc).

After the first blocked amino acid has been covalently attached to the polymer resin, its blocking group is removed with, for example, trifluoroacetic acid (TFA) for Boc or piperidine for Fmoc. This is followed by reaction of the unblocked amine group of the first amino acid with the carboxyl group of a second blocked amino acid in the presence of a suitable coupling agent, for example, dicyclohexylcarbodiimide (DCC), to form a dipeptide.

The process is then repeated until the desired polypeptide is produced, whereupon the polypeptide is chemically cleaved with liquid hydrofluoric acid, $HF_{liq}$ or TFA, for example.

Polymeric resins for use in the solid phase synthesis are commercially available and well know to those skilled in the art. A representative example that has been advantageously employed in the practice of the present invention is FMOC Amino Acids-p-Alkoxybenzyl Alcohol Resins, supplied by Bachem Fine Chemicals, Inc. of Torrance, Calif. Such resins contain 1% cross-linked divinylbenzene-styrene with substitution levels of about 0.3–0.5 mmol/g, 200–400 mesh.

In the practice of the present invention, the above-described solid phase synthesis procedures are preferably used. Prior to the initiation of the synthesis, however, the location along the proposed polypeptide chain of one or more desired sites for the covalent attachment of the PAG, whether directly or through intervening groups, is pre-determined. The synthesis of the polypeptide is then begun, as described above, and continued until the point is reached which corresponds to the predetermined site. At this point, the polymer is added preferably with a facilitator moiety. In the case of an amino acid facilitator, the next amino acid to be added will include the PAG in the form of a facilitator-polymer conjugate. For convenience, this next-to-be-added amino acid will be referred to herein as the Specific Site Amino Acid ("SSAA"). It is to be understood that non-amino acid facilitator conjugates such as those containing functionalized alkyl moieties are added in the same manner. After the polymer is added, the sequential formation of the polypeptide continues until the polypeptide is completed.

The SSAA can be any amino acid known in the art having one or more reactive groups in addition to the amino and carboxyl groups that are attached to the α carbon atom. Amino acids that can be employed as the SSAA in the practice of the present invention include, for example, arginine, glutamic acid, lysine, aspartic acid, cysteine, histidine, tryptophan, tyrosine, asparagine glutamine, serine, threonine, and the like. The preferred amino acids for use as the SSAA are arginine, glutamic acid, lysine, aspartic acid, cysteine, serine, and threonine. Lysine is the most preferred amino acid. The only limitation on the selection of amino acid is that it contains a moiety which can conjugate with a properly functionalized polymer.

In one embodiment of the present invention, the SSAA, at the time of its addition to the partially synthesized polypeptide chain, has already been covalently bonded to PAG via one of the SSAA's reactive groups that is not attached to the α carbon atom, either directly or indirectly through intervening chemical groups. The α amino group and any additional reactive groups not intended for reaction at this point in the synthesis are blocked with known blocking agents in the usual fashion. The blocked, pegylated SSAA is then attached to the partially grown polypeptide chain as described above. N-α-Fmoc-N-ε-PEG-β-Ala-Lys or N-α-Fmoc-N-ε-PEG-Lys are examples of preferred blocked amino acids.

In another embodiment of the present invention, the specific predetermined site has not been previously reacted with the PAG, but, rather, the α amino group and all the additional reactive groups, other than the α carboxyl group are blocked. The blocked SSAA is then attached to the partially grown polypeptide chain as described above. Pegylation is carried out by solid phase synthesis except that the blocking group, i.e. Fmoc, is left on the terminal amine, or α terminal. At this time, after cleavage of the fully grown polypeptide from the polymeric resin, the reactive group(s) of the SSAA residue in the chain is (are) blocked—the α-$NH_2$ group remaining blocked—and subsequently pegylated.

Those skilled in the are will understand that, if desired, the terminal amino and/or carboxyl groups of the thus prepared polypeptide can also be pegylated. After completion of the synthesis, but prior to cleavage from the polymeric resin, the terminal $NH_2$ group is deblocked and then pegylated. Thereafter, it is cleaved from the resin with TFA or HF$_{liq}$.

It will also be clear, of course, that more than one SSAA can be included in the synthesized polypeptide by the process of the present invention. The conjugates may have from 1 or several polymeric strands attached to the synthesized polypeptide, depending, inter alia, upon the length of the polypeptide chain and the desired properties of the finished product.

The method of the present invention will permit the site specific introduction into a polypeptide of any number of pegylated amino acid residues—from one up to several hundred, if desired.

Having now generally described this invention, it will be better understood by reference to certain specific examples, which are included for purposes of illustration only and are not intended to be limited unless otherwise specified.

EXAMPLES

Example 1

Preparation of Methoxypoly(ethylene glycol)-succinimidyl carbonate (SC-PEG)

Dissolve 60 g of methoxy poly(ethylene glycol) molecular weight 5,000 in 200 ml of 3/1 toluene/dichloromethane and treat with a toluene solution of phosgene (30 ml, 57 mmol) overnight. Evaporate the solution to dryness and remove the remainder of the phosgene under vacuum. Redissolve the residue in 150 ml of 2/1 toluene/dichloromethane. Treat the resulting solution with 2.1 g (18 mmol) of solid N-hydroxysuccinimide, followed by 1.7 ml (12 mmol) of triethylamine. Allow the solution to stand for three hours and then filter it and evaporate it to dryness. Dissolve the residue in 600 ml of warm (50° C.) ethyl acetate, filter the solution. and cool it to facilitate precipitation of the polymer. Collect the product by filtration, then recrystallize from ethyl acetate, and dry under vacuum over P$_2$O$_5$.

Example 2

Synthesis of N-α-Fmoc-N-ε-PEG-Lys Using Succinimidyl Carbonate Methoxy Poly(ethylene glycol) (SC-PEG)

A mixture of 0.25 g (0.678 mole) N-α-Fmoc-Lys and 3.39 g (0.678 mmole) SC-PEG was placed in a 50 ml round bottom flask. To this was added 6.2 ml of acetonitrile, 1.3 ml of dimethylformamide, and, finally 2.5 ml of borate buffer at pH 9.0. The mixture was stirred vigorously for three hours at room temperature using a stir bar to help dissolve the N-α-Fmoc-Lys. At one hour and two hours, small particles of N-α-Fmoc-Lys had to be crushed using a Teflon stirring rod. Such crushing of the N-α-Fmoc-Lys to a powder form led to a completely homogeneous mixture at two hours reaction time. At the end of the reaction (three hours), 10 ml of 2-propanol was added as the mixture was stirring. The resulting solution was dropped slowly into 450 ml of ether with stirring. The product precipitated instantaneously and was filtered off on a 150 ml medium size fritted funnel and dried under vacuum overnight. Yield: 3.34 g (91.8%).

Example 3

Synthesis of N-α-Fmoc-N-ε-PEG-β-Ala-Lys

To a mixture of 2.5 g of PEG-β-Ala (0.5 mmole), 0.221 g benzotriazolyloxy-trisdimethylaminophosphoniumhexafluorophosphate (BOP) (0.5mmole) and 0.076 g 1-hydroxybenzotriazole hydrate (HOBt) (0.5 mmole) was added 2.5 ml of methylene chloride followed by 2.5 ml of dimethyl formamide. 110 μl of N-methylmorpholine was then added to make a 0.2M solution. The preparation of PEG-β-Ala is described in PCT Publication WO 92/16555, the disclosure of which is incorporated herein by reference. The homogeneous solution thus obtained was stirred for ten minutes, during which time its color turned slightly yellowish. 0.185 g of N-α-Fmoc-Lys (0.5 mmole) was added to the activated PEG-β-Ala. Initially, the N-α-Fmoc-Lys was insoluble, but, as the reaction proceeded with stirring at room temperature, it went into solution. After forty-five minutes, most of the N-α-Fmoc-Lys was in solution except for a few large lumps that had to be broken down with a glass rod. After 1.5 hours, the solution was homogeneous and the color was deep orange-yellow. After two hours of stirring, the reaction mixture was dropped slowly, with stirring into 250 ml of cold diethyl ether. A white precipitate formed, which was filtered on a medium size fritted funnel, washed twice with 15 ml of ether, and dried under vacuum. The product was recrystallized from 2-propanol at 50° C., washed with cold 2-propanol and finally with ether and then dried under vacuum. The product was characterized with $^1$H-NMR and $^{13}$C-NMR in dimethyl sulfoxide. It was completely soluble in methylene chloride and dimethyl sulfoxide, unlike the N-α-Fmoc-Lys starting material, which has very poor solubility in organic solvents. Owing to the attachment of PEG, the solubility changes. Yield: 59 based upon N-α-Fmoc-Lys.

Example 4

Synthesis of Tyr-N-ε-PEG-β-Ala-Lys-Pro Using the Product of Example 3 (hereinafter, for convenience, "PRODEX-3")

A Milligen 9600 Peptide Synthesizer was set up for a regular synthesis, with some modifications. N-α-Fmoc-Pro resin (0.2 g, 0.42 mmole/g) was placed in the reaction vessel. In the first reservoir were placed 1.4 g of PRODEX-3 (Mol. Wt. 5386 g/mole, 0.26 mmole, 0.052M final concentration), 0.04 g HOBt (0.26 mmole) and 0.175 g BOP (0.26 mmole). The coupling time of PRODEX-3 to proline was increased to two hours. The PRODEX-3 went into solution in 0.17M N-methylmorpholine in CH$_2$Cl$_2$/DMF and was transferred with no problems (i.e., no clogging due to the viscosity of the PEG). N-α-Fmoc-Tyr was added as usual. The end resin was dried under vacuum for three days. The weight of the resin increased from 0.2 g to 0.37 g owing to the attachment of the PEG. This increase amounts to 73% coupling at the PRODEX-3 coupling step.

The peptide was cleaved from the resin with 2.5 ml of 95% TFA, 5% liquified phenol under He$_{(g)}$ for two hours. The TFA was evaporated off under vacuum yielding on oily, thick residue (phenol and product), which was diluted with 2.0 ml of methanol and then dropped slowly with stirring into cold ether. Although the native tripeptide is too small to precipitate out of ether, the PEG modified tripeptide precipitated out readily and was filtered off on medium size fritted funnel, washed with ether, and dried under vacuum. It was characterized by amino acid sequence analysis, which confirmed the sequence Tyr-(no residue)-Pro.

EXAMPLE 5

Pegylation of PLAP Peptide at Lys⁷ Only

The amino acid sequence of a phospholipase $A_2$ activating peptide (PLAP) [SEQ ID NO: 1:]is:

Glu-Ser-Pro-Leu-Ile-Ala-Lys-Val-Leu-Thr-Thr-Glu-Pro-Pro-Ile-Ile-Thr-Pro-Val-Arg-Arg

This PLAP peptide was synthesized, de-protected, and removed form the resin using the Milligen 9600 Peptide Synthesizer. The peptide was not deblocked (i.e., the N-terminal Fmoc protection group was retained). In [N-α-Fmoc-Glu¹]-PLAP peptide, the only site for pegylation would be the ε-$NH_2$ in Lys⁷. The pegylation using SC-PEG was carried out as follows: [N-α-Fmoc-Glu¹]-PLAP (4.3 mg, 1.7 μmole) was dissolved in 500 μl of borate buffer at pH 9.0 in an Eppendorf tube and then 34 mg of SC-PEG (6.8 μmole) was added. The reaction was stirred at room temperature and monitored on reverse phase HPLC. The pegylated product was purified on a semi-preparative $C_{18}$ column and lyophilized to dryness. The product, [N-α-Fmoc-Glu¹-N-ε-PEG-Lys⁷]-PLAP, was treated with 500 μl of 30% piperidine in DMF for fifteen minutes. This reaction was monitored on reverse-phase HPLC, which indicated the removal of the Fmoc group by the shift of the product peak to a lower retention time. This product was purified on a semi-preparative reverse-phase column, concentrated, and lyophilized to dryness. It was characterized as [N-ε-PEG-Lys⁷]-PLAP peptide by sequence analysis.

EXAMPLE 6

Example 5 is repeated except that instead of the conjugated phospholipase $A_2$ activating peptide (PLAP) synthesized therein, the following conjugated polypeptides are synthesized with equivalent results:

A. [N-ε-PEG-Lys¹¹]-Dynorphin A
B. [N-ε-PEG-Lys⁷]-α-neo-endorphin
C. [N-ε-PEG-Lys⁷]-β-neo-endorphin where the amino acid sequence of:

A. Dynorphin A is [SEQ ID NO: 2:]: Tyr-Gly-Gly-Phe-Leu-Arg-Arg-Ile-Arg-Pro-Lys-Leu-Lys;

B. α-neo-endorphin is [SEQ ID NO: 3:]: Tyr-Gly-Gly-Phe-Leu-Arg-Lys-Tyr-Pro-Lys; and C. β-neo-endorphin is [SEQ ID NO: 4]: Tyr-Gly-Gly-Phe-Leu-Arg-Lys-Tyr-Pro.

Although the foregoing refers to particular preferred embodiments, it will be understood that the present invention is not so limited. It will occur to those skilled in the art that various modifications may be made to the disclosed embodiments and that such modifications are intended to be within the scope of the present invention.

---

What is claimed is:

1. A method of synthesizing a polypeptide containing a substantially non-antigenic polymer at one or more predetermined sites within said polypeptide, said method comprising:
   a) initiating synthesis of the amino acid chain of said polypeptide;
   b) conjugating a substantially non-antigenic polymer to a facilitator moiety;
   c) introducing said conjugated polymer at each point in the synthesis which corresponds to each said predetermined site; and
   d) continuing said synthesis of said amino acid chain of said polypeptide.

2. The method of claim 1, wherein said synthesis is solid-phase synthesis.

3. The method of claim 1, wherein said facilitator moiety comprises an amino acid.

4. The method of claim 3, wherein said facilitator-polymer conjugate is amino acid N-α-Fmoc-N-ε-PEG-Lys.

5. The method of claim 3, wherein said facilitator-polymer conjugate is amino acid N-α-Fmoc-N-ε-PEG-β-Ala-Lys.

6. The method of claim 3, wherein said amino acid is selected from the group consisting of arginine, glutamic acid, lysine, aspartic acid, cysteine, histidine, tryptophan, tyrosine, asparagine, glutamine, serine and threonine.

7. The method of claim 1, wherein said polymer is a poly(alkylene glycol).

8. The method of claim 7, wherein said polymer comprises polyethylene glycol.

9. The method of claim 7, wherein said poly(alkylene glycol) comprises polyethylene glycol succinimidyl succinate.

10. The method of claim 7, wherein said poly(alkylene glycol) comprises methoxy poly(ethylene glycol)-succinyl carbonate.

11. The method of claim 1, wherein said polymer has a molecular weight of from 200 to about 10,000.

12. The method of claim 11, wherein said polymer has a molecular weight of from 2,000 to about 7,500.

13. The method of claim 12, wherein said polymer has a molecular weight of 5,000.

14. The method of claim 1, wherein said polypeptide is phospholipase $A_2$ activating peptide.

15. The method of claim 1, wherein said polypeptide is selected from the group consisting of dynorphin A, α-neo-endorphin, β-neo-endorphin, melittin, mastoparan, vasopressin, oxytocin, opioid peptides, kinins, angiotensin, luteinizing hormone releasing hormone, corticotropin releasing hormone, calcitonin, and thyrotropin releasing hormone.

16. The method of claim 1, wherein said polypeptide has an affinity for a target in a range of from $1 \times 10^{-7}$ to $1 \times 10^{-11}$ M.

17. The method of claim 1, wherein said polymer is selected from the group consisting of dextran, polyvinyl pyrrolidones, polysaccharides, starches, polyvinyl alcohols, polyacrylamides and other substantially non-antigenic polymers.

18. The method of claim 1, wherein said facilitator moiety is selected from the group consisting of alkyls and substituted alkyls.

19. A method of synthesizing a polypeptide containing a substantially non-antigenic polymer at one or more predetermined sites within said polypeptide, said method comprising:
   a) initiating synthesis of the amino acid chain of said polypeptide;
   b) introducing a blocked facilitator moiety at that point in the synthesis that corresponds to each said predetermined site;
   c) completing the synthesis of said amino acid chain of said polypeptide; and
   d) deblocking and conjugating the facilitator moiety with said non-antigenic polymer.

20. The method of claim 19, wherein said synthesis is solid phase synthesis.

21. The method of claim 19, wherein said facilitator moiety comprises an amino acid.

22. The method of claim 21, wherein said amino acid is selected from the group consisting of arginine, glutamic acid, lysine, aspartic acid, cysteine, histidine, tryptophan, tyrosine, asparagine, glutamine, serine and threonine.

23. The method of claim 19, wherein said polymer is a poly(alkylene glycol).

24. The method of claim 23, wherein said polymer comprises polyethylene glycol.

25. The method of claim 19, wherein said polypeptide is phospholipase $A_2$ activating peptide.

26. The method of claim 19, wherein said polypeptide is selected from the group consisting of dynorphin A, α-neo-endorphin, β-neo-endorphin, melittin, mastoparan, vasopressin, oxytocin, opioid peptides, kinins, angiotensin, luteinizing hormone releasing hormone, corticotropin releasing hormone, calcitonin, and thyrotropin releasing hormone.

27. The method of claim 19, wherein said polymer has a molecular weight of from 200 to 10,000.

28. The method of claim 19, wherein said polymer is selected from the group consisting of dextran, polyvinyl pyrrolidones, polysaccharides, starches, polyvinyl alcohols polyacrylamides and other substantially non-antigenic polymer substances.

29. The method of claim 19, wherein said facilitator moiety is selected from the group consisting of alkyls and substituted alkyls.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear ( x i ) SEQUENCE DESCRIPTION: SEQ ID NO:1:

```
Glu  Ser  Pro  Leu  Ile  Ala  Lys  Val  Leu  Thr  Thr  Glu  Pro  Pro  Ile
 1              5                            10                           15
Ile  Thr  Pro  Val  Arg  Arg
                20
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:2:

```
Tyr  Gly  Gly  Phe  Leu  Arg  Arg  Ile  Arg  Pro  Lys  Leu  Lys
 1              5                            10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:3:

```
Tyr  Gly  Gly  Phe  Leu  Arg  Lys  Tyr  Pro  Lys
 1              5                            10
```

(2) INFORMATION FOR SEQ ID NO:4:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:4:

Tyr Gly Gly Phe Leu Arg Lys Tyr Pro
1                5